US009833319B2

(12) United States Patent
Gerber et al.

(10) Patent No.: US 9,833,319 B2
(45) Date of Patent: Dec. 5, 2017

(54) OSTEOCONDUCTIVE COATING OF IMPLANTS MADE OF PLASTIC

(71) Applicant: Thomas Gerber, Papendorf (DE)

(72) Inventors: Thomas Gerber, Papendorf (DE); Holger Keuer, Rostock (DE)

(73) Assignee: Thomas Gerber, Papendorf (DE)

( * ) Notice: Subject to any disclaimer, the term of this patent is extended or adjusted under 35 U.S.C. 154(b) by 0 days.

(21) Appl. No.: 14/436,598

(22) PCT Filed: Oct. 18, 2013

(86) PCT No.: PCT/EP2013/071878
§ 371 (c)(1),
(2) Date: Apr. 17, 2015

(87) PCT Pub. No.: WO2014/060591
PCT Pub. Date: Apr. 24, 2014

(65) Prior Publication Data
US 2016/0166386 A1    Jun. 16, 2016

(30) Foreign Application Priority Data

Oct. 19, 2012 (DE) .................. 10 2012 020 603

(51) Int. Cl.
*C04B 35/447* (2006.01)
*A61L 24/00* (2006.01)
(Continued)

(52) U.S. Cl.
CPC ............ *A61F 2/2846* (2013.01); *A61L 27/18* (2013.01); *A61L 27/306* (2013.01); *A61L 27/32* (2013.01);
(Continued)

(58) Field of Classification Search
CPC .... C04B 35/447; C04B 35/46; A61L 24/0036
(Continued)

(56) References Cited

U.S. PATENT DOCUMENTS

| 6,602,293 | B1 | 8/2003 | Biermann et al. |
| 2005/0228498 | A1* | 10/2005 | Andres ................. A61F 2/4465 623/17.11 |
| 2007/0059379 | A1* | 3/2007 | Gerber ..................... A61L 27/12 424/602 |

(Continued)

FOREIGN PATENT DOCUMENTS

| DE | 102006037497 A1 * | 2/2008 | ............ A61K 33/00 |
| DE | 102008044951 A1 | 8/2009 | |
| EP | 1624904 B1 | 1/2007 | |
| EP | 2238992 A1 | 10/2010 | |

OTHER PUBLICATIONS

International Search Report dated Jan. 23, 2014 from PCT/EP2013/071878 (3 pages).

*Primary Examiner* — Cachet Sellman
(74) *Attorney, Agent, or Firm* — Hovey Williams LLP

(57) ABSTRACT

The invention relates to biomaterials based on plastics, such as polyaryl polyether ketone (PEK), and to methods for producing and using same. The following describes how a mechanically stable coating made of a porous bone substitute material, e.g. Nano Bone®, is applied to polyaryl polyether ketone (PEK), e.g. polyether ether ketone (PEEK), as a result of which the problem of poor cell adhesion on plastics surfaces of this kind can be solved. The bone substitute material can be applied both dry as a powder and also in a wet spraying method. The coating is a result of briefly melting the polymer surface and the resulting partial penetration of the previously applied layer. In the process, the molten polymer penetrates into nanopores of the bone substitute material and thus establishes a firm connection.

10 Claims, 7 Drawing Sheets

(51) Int. Cl.
  *A61F 2/28* (2006.01)
  *A61L 27/30* (2006.01)
  *A61L 27/32* (2006.01)
  *A61L 27/56* (2006.01)
  *A61L 27/18* (2006.01)
  *A61L 27/34* (2006.01)
  *A61L 27/42* (2006.01)
  *A61L 27/54* (2006.01)

(52) U.S. Cl.
  CPC .............. *A61L 27/34* (2013.01); *A61L 27/425* (2013.01); *A61L 27/54* (2013.01); *A61L 27/56* (2013.01); *A61L 2400/18* (2013.01); *A61L 2420/02* (2013.01); *A61L 2420/04* (2013.01); *A61L 2420/06* (2013.01); *A61L 2430/02* (2013.01); *A61L 2430/38* (2013.01); *C08G 2650/40* (2013.01)

(58) Field of Classification Search
  USPC .......................................... 623/17.11; 264/5
  See application file for complete search history.

(56) References Cited

U.S. PATENT DOCUMENTS

| | | | |
|---|---|---|---|
| 2009/0001622 A1* | 1/2009 | Nader | A61F 2/30942 264/5 |
| 2009/0276053 A1* | 11/2009 | Brown | A61F 2/2846 623/18.11 |
| 2010/0082072 A1* | 4/2010 | Sybert | A61B 17/68 606/326 |

\* cited by examiner

6 μm

A

B

OSTEOCONDUCTIVE COATING OF IMPLANTS MADE OF PLASTIC

RELATED APPLICATIONS

This application is the National Stage of International Patent Application No. PCT/EP2013/071878, filed Oct. 18, 2013, which is hereby incorporated by reference in its entirety, and which claims priority to German Patent Application No. 10 2012 020 603.8, filed Oct. 19, 2012.

The invention relates to biomaterials based on plastics such as polyaryl polyether ketone (PEK) and to methods for their manufacture and use. The following describes how a mechanically stable coating is made on polyaryl polyether ketone (PEK), such as polyether ether ketone (PEEK) with a porous bone substitute material such as NanoBone®, as a result of which the problem of poor cell adhesion on plastic surfaces of this kind can be solved. The application of the bone substitute material can be made either dry as a powder or in a wet spraying method. The coating is a result of briefly melting the polymer surface and the resulting partial sinking of the previously applied layer. In the process, the molten polymer penetrates into nanopores of the bone substitute material and, thereby, establishes a firm connection.

Biomaterials on the basis of e.g. polyether ether ketone (PEEK) have gained great importance for implants in trauma surgery, orthopedics and in particular in spinal surgery in the last 30 years. This is a result of the excellent mechanical properties and the good biocompatibility.

A limitation is the limited fixation of PEEK in the bone, i.e. the PEEK forms a poor connection with the bone ("PEEK Biomaterials in Trauma, Orthopedic, and Spinal Implants", S. M. Kutz and J. N. Devine; Biomaterials, 2007 Nov., 28(32):4845-4869).

Many efforts were therefore directed at circumventing the poor cell-PEEK adhesion and thereby improving the bone-implant-junction.

For this purpose, composites made from PEEK and calcium phosphate biomaterials, such as hydroxyapatite (HA) and tricalcium phosphate (β-TCP), have been developed. Disadvantages of these composites are their worse mechanical properties and the phenomenon that the ceramic biomaterial and the plastic PEEK do not form a connection ("Tension-tension fatigue behavior of hydroxyapatite reinforced polyetheretherketone composites" S. M. Tang et al. Int J Fatigue 2004; 26; 49-57).

Another path to improve the bone-implant-contact was explored with different coatings (for example: Cook S D, Rust-Dawicki A M. Preliminary evaluation of titanium-coated PEEK dental implants. Journal of oral implantology 1995; 21(3):176-181; Ha S, Mayer J, Koch B, Wintermantel E. Plasma-sprayed hydroxylapatite coating on carbon fibre reinforced thermoplastic composite materials. J Mat Sci 1994; 5:481-484).

Chemical modifications of the PEEK surface were also developed (for example: Noiset O, Schneider Y J, Marchand-Brynaert J. Adhesion and growth of CaCo2 cells on surface modified PEEK substrata. Journal of biomaterials science Polymer edition 2002; 11(7):767-786 and Noiset O, Schneider Y J, Marchand-Brynaert J. Fibronectin adsorption or/and covalent grafting on chemically modified PEEK film surfaces. J Biomater Sci Polym Ed 1999; 10(6):657-677).

Known are PEEK implants with calcium phosphate (S.-W. Ha et al.; Surface activation of polyetheretherketone (PEEK) and formation of calcium phosphate coatings by precipitation. JOURNAL OF MATERIALS SCIENCE MATERIALS IN MEDICINE 8 (1997) 683-690) or titanium plasma spray coated surfaces (C.-M. Han et al.; The electron beam deposition of titanium on polyetheretherketone (PEEK) and the resulting enhanced biological properties. BIOMATERIALS 31 (2010) 3465-3470) and a titanium coating with subsequent calcium phosphate coating (S.-W. Ha et al.; Topological characterization and micro structural interface analysis of vacuum-plasma-sprayed titanium and hydroxyapatite coatings on carbon fibre-reinforced poly (etheretherketone). JOURNAL OF MATERIALS SCIENCE MATERIALS IN MEDICINE 8 (1997) 891-896). A disadvantage of the layers produced by plasma spray is that these layers are relatively thick and that there is a risk that they flake off as a result of mechanical influences, such as upon implantation of the implant.

For example, S.-W. Ha shows that the adhesion between PEEK and the HA layer is very low (S.-W. Ha et al.; Plasma-sprayed hydroxylapatite coating on carbon fibre reinforced thermoplastic composite materials. JOURNAL OF MATERIALS SCIENCE MATERIALS IN MEDICINE 5 (1994) 481-484).

This abrasion of the implant layer has a negative effect on the surrounding tissue. Metal titanium particles in particular show negative effects. The positive bioactive properties of the titanium are ultimately caused by the oxide layer on the surface. Moreover, a flaking off or a degradation of the coated layer again entails a poor cell-PEEK contact area.

The problem to be solved by the invention is to modify the surface of PEEK implants in such a manner that a good interface between bones and implants develops. This modification shall neither negatively influence the mechanical properties of the implant nor influence an in vivo application, such as by surface areas that are flaking off.

Solving this problem is supported by the following surprising observation. When a granulate of a highly porous silica gel, into which HA is embedded, is placed on a PEEK surface and the surface is molten, the liquid PEEK enters the nanopores of the silica gel and the granulate sinks partially in the molten PEEK.

Therefore, the invention relates to a plastic implant, in which a highly porous bone substitute material is embedded in the surface layer in the plastic in the area or the areas wherein the bone is to grow onto the implant, wherein the bone substitute material protrudes from the surface of the bone replacement material. The porosity of the bone substitute material is preferably in the range of 20 to 80% and/or the average pore size (of the bone substitute material) is preferably in the range of 10 to 100 nm. The surface layer of the plastic has preferably a thickness of 1 μm to 100 μm and/or the bone substitute material protrudes from the plastic in the range of from 0.01 μm-50 μm, more preferably in the range of from 0.1 to 30 μm or in the range of from 1 to 20 μm.

Preferably, the bone substitute material is crystalline hydroxyapatite (HA) embedded in an amorphous porous silica matrix, wherein the HA has a share of from 20 to 90% by weight in terms of HA and silica, is a granulate with a size that is preferably in the range from 1 to 50 μm or a continuous layer with a preferred layer thickness of from 1 to 20 μm.

As granulate, a bone substitute material described by the patent EP 1624904 B1 is used. EP 1624904 B1 discloses a granulate based on calcium phosphate, in which crystalline calcium phosphate is embedded in a silica xerogel matrix. This is obtainable by manufacture of the calcium phosphate via a precipitation reaction during which the solution with the precipitated calcium phosphate is homogenized, e.g. by stirring, a highly concentrated silica solution is added, the mixture is fixated by the subsequently starting gelation and it is transferred into a xerogel matrix by removal of the solvent. The calcium phosphate crystallites comprised in the xerogel matrix have a size of about 10 nm to about 2000 nm and the granules have a size of about 1 μm to about 1000 μm, and the share of the silicon dioxide is in the range of about 2 to about 80% by weight, preferably in the range of about 4 to about 50% by weight, in terms of the total mass of the granules. EP 1624904B1 further discloses a material with granules which comprise individual hydroxyapatite crystallites, which are embedded in a silicon dioxide xerogel matrix and are surrounded by it, wherein the individual hydroxyapatite crystallites have a size of about 10 nm to about 2000 nm and are homogenously distributed in the matrix, wherein the granules have a size of about 1 μm to about 1000 μm, and wherein the silicon dioxide accounts for about 2 to about 80% by weight of the total mass of the granules. A bone substitute material is further disclosed in EP 1624904B1, which comprises granules of this granulate, which form a three-dimensional structure which comprises pores of approximately the size of the granules in addition to the pores in the granules. In consequence, the bone replacement material is highly porous.

Bone substitute material of this sort are commercially available inter alia as NanoBone® (Artoss GmbH, Rostock, Germany). Nevertheless, other porous bone substitute materials can also be used, such as Bio-Oss® of the Geistlich Pharma AG, Germany. The bone substitute materials have preferably a high porosity (preferably about 10% to about 90%, in particular about 20% to about 80% or about 40% to about 80%, about 50% to about 70%).

Porosity can e.g. be measured with the standard mercury porosimetry method.

The material used has an inner surface of about 200 m²/g (measured with gas adsorption (BET)). The porosity was about 60%, wherein the pore size of from a few nanometers to 20 nm is predominant.

The plastic polyether ether ketone (PEEK) is preferred, however, e.g. polyaryl polyether ketone (PEK), in particular polyether ketone (PEKK), can also be used.

The plastic in the implant according to the invention has penetrated into nanopores of the bone substitute material. In particular nanopores of the bone substitute material in a surface layer of the plastic are filled with the same, in a manner that causes development of a composite of plastic and bone substitute material having a thickness of several micrometers at the junction between the plastic implant and the bone substitute material (in the surface layer).

Subject of the invention is a method for the manufacture of a plastic implant according to the invention, wherein a mold, such as the mold for the manufacture of the implant, is coated with an aqueous slurry of a highly porous bone substitute material (as described above) in the areas in which the implant is to have contact with the bone (or in which the bone is to grow onto the implant), wherein the layer is dried and the plasticized plastic is subsequently introduced into the mold. Subsequently the surface of the plastic is heated or molten. For example, inductive heating of the metal mold for the implant up to 300-500° C. may be used, preferably 380-400° C., as measured at the surface of the mold, for about 3 to about 20 seconds, preferably 5-10 seconds (e.g. with TIG 30/100, HUTTINGER Elektronik GmbH). A hot air stream may also be used, e.g. in the case of a non-metal mold.

The slurry consists preferably of water and a crystalline hydroxyapatite (HA) granulate, embedded in an amorphous porous silicon dioxide matrix, wherein the size of the granulate is preferably in the range of about 1 to 50 μm or about 5 to 10 μm, e.g. smaller than 10 μm.

With the effect observed an entire mold body can be coated. When the bone substitute material described is ground and sieved, so that granules that are preferably smaller than 10 μm remain, and when a slurry is generated with water from this, a mold can be coated and dried. When the plasticized plastic is subsequently deposited into the mold, the above described effect occurs. The plastic penetrates into the nanopores. In a surface layer a composite develops from plastic and silica gel/HA. The Silica/HA material finally predominates at the surface.

As shown in examples 1 and 2, a perfect contact between PEEK implant and the bone is achieved thereby.

A second method can e.g. be used in case the molding of the implant is supposed to be independent of the surface modification. Rotationally symmetric as well as not rotationally symmetric implants can be coated. In this case one does not have to rely on a bone substitute material previously produced.

The essence of this method is a sol-gel coating process.

Subject of the invention is, therefore, also a method for the manufacture of a plastic implant according to the invention, in which
the areas of the implant onto which the bone is to grow are hydrophilized, such as by an oxygen plasma, wherein e.g. a low pressure plasma chamber or a plasma jet under normal pressure can be used,
a silicon dioxide sol, into which crystalline hydroxyapatite is going to be dispersed or is dispersed, is applied to the areas of the implant that have been hydrophilized, wherein the solid matter concentration (HA and $SiO_2$) of the sol is in the range of 0.2 to 10% by weight and the ratio of HA to $SiO_2$ is in the range of from 90 to 10% by weight to 40 to 60% by weight, e.g. by means of dip coating, spin coating or spray coating,
the layer thus obtained is dried, and
the plastic implant surface is subsequently heated to an extend that the molten plastic penetrates into pores of the layer that developed or was coated, in particular in nanopores.

The silicon dioxide sol is manufactured with the dispersed hydroxyapatite in a manner that uses sodium hydrogen phosphate and calcium chloride for precipitation of HA, that, e.g. by rinsing and filtering, the concentration of the sodium and chlorine ions is lowered, wherein the ion concentration is preferably lowered to less than 0.1% of the initial concentration, that, e.g. by adding and filtering of ethanol, the water content is reduced, wherein the water content (after) is preferably less than 1% of the total solvent, that by hydrolyzing tetraethyl orthosilicate (TEOS) with the preferred use of an organic acid as catalyst, particularly preferred acetic acid, a silica sol is generated that is mixed with the hydroxyapatite suspension.

In the second method according to the invention, the surface is, thus, hydrophilized, e.g. by means of an oxygen plasma, to facilitate the coating of the plastic implant. A normal pressure plasma jet (e.g. with Plasma Beam, diener electronic GmbH) or low pressure plasma (e.g. with Nano PCCE, diener electronic GmbH) can be used for this purpose. A silica sol into which crystalline HA is dispersed is manufactured for the coating. The solid matter concentration (HA and $SiO_2$) of the sol is to be in the range of 0.2-10% by weight. The ratio of HA to $SiO_2$ is determined to be in the range of from 90-10% by weight to 40-60% by weight. For example by means of dip-coating, spin-coating or spray-coating the areas of the implants onto which bone is supposed to grow can now be coated. The further areas of the implant can for example be covered. The layer is dried. The procedure can be repeated multiple times if necessary (e.g. twice, three times, four times or five times) to generate an appropriate thickness of the layer. The inner construction of the layer up into the nanometer region is now comparable with the above described bone substitute material and corresponds to the bone substitute material according to EP 16249041 B1, respectively.

Optionally, the layer of silicon dioxide and HA can be activated by means of a oxygen plasma prior to the heating of the plastic surface.

Subsequently, the plastic implant surface is heated to an extent that the plastic penetrates into the pores, in particular nanopores, of the resulting layer. This can e.g. occur with a hot airstream (e.g. about 300-400° C., preferably about 350-380° C. for about 2-30 seconds, preferably 5-20 or 10-15 seconds). The layer practically sinks in the plastic to an extent that only the upper part protrudes.

After cooling, the surface can again be treated with oxygen plasma, to remove organic remains which can stem from the sol if necessary. In case activation with oxygen plasma has occurred after the coating and prior to the heating, a second treatment is not necessary. Depending e.g. on the storage and the purpose one can however also refrain from both treatments with oxygen plasma after the coating of the implant.

If desired, a further layer of bone substitute material can be applied onto the layer of bone substitute material according to the invention that is already partially molten down. For this purpose a silicon dioxide sol can be applied to the areas of the implant on which a thicker layer of bone substitute material, which protrudes from the plastic, is desired, e.g. by means of dip-coating, spin-coating or spray-coating, wherein crystalline hydroxyapatite is dispersed in the silicon dioxide sol. This can e.g. be useful in case due to the form of the implant sinking of the layer is uneven.

A further subject of the present invention is also a plastic implant, in particular a not rotationally symmetric plastic im-plant, producible or produced according to this second method. This differs from implants coated according to the invention that were manufactured according to the first method in that not granules of the bone substitute material are partially embedded in the plastic but that a homogenous layer of the bone substitute material is embedded partially in the plastic.

Subject of the invention is also a plastic implant, preferably made of PEK, PEKK or in particular PEEK, in which in those areas in which bones are to grow onto the implant, a homogenous layer of a bone substitute material is embedded in the surface layer of the plastic, wherein the bone substitute material protrudes from the surface. In this case homogenous pertains to the homogenous distribution of the bone substitute material in the direction of the plastic surface. In vertical direction thereto, such as shown in FIG. 6B no homogeneity can be found, but the plastic portion increases in the direction of the im-plant. Such a plastic implant can e.g. be manufactured with the second method according to the invention. The porosity of the bone substitute material is preferably in the range of 20-80, i.e. the bone substitute material is highly porous, and/or the average pore size (of the bone substitute material) is preferably in the range of 10-100 nanometers. The surface layer of the plastic has preferably a thickness of 1 µm-100 µm and/or the bone substitute material protrudes in the range of 0.01 µm-50 µm, more preferably in the range of 0.1-30 µm or in the range of 1-20 µm from the plastic.

The invention relates also to a plastic implant producible or produced according to the above described first method, in particular to a rotationally symmetric plastic implant.

Of course, a plastic implant may also be coated on its entire surface with the methods according to the invention, in case it is e.g. to have contact to the bone on the entire surface after implantation, such as in the case of a cage for the fusion of vertebrae.

Due to the penetration of the nanopores with the plastic, the surface layer is mechanically highly stable. No additional layer has to exists on the plastic silica gel/HA composite for the interaction of tissue, i.e. it is sufficient if the bone substitute material is at the surface, it does not necessarily have to protrude. Depending on the efficacy of the material an additional layer is, however, advantageous. Due to the novel nanostructured surface of the PEEK, a complete degradation of the lowest bone substitute material layer by bone degrading cells is prevented, because these cannot enter this structure. Finally, a thin layer of biomaterial is retained on the PEEK surface.

Subject of the invention is further the use of a plastic implant according to the invention for implantation, in particular as implant with implant-bone contact, preferably in the trauma surgery, the orthopedics, and/or in particular the spinal surgery. The plastic implant can e.g. be a cage, an implant for spinal fusion. Tooth implants coated according to the invention may also be used.

Animal experiments demonstrate an improvement of the bone-implant-contact by up to 15% for implants according to the invention in comparison with corresponding conventional plastic implants that are not coated and, thus, prove the advantages of the invention.

LEGEND

FIG. 1 shows a layer of the bone replacement material manufactured according to example 1 which is partially sunken in PEEK. Scale: 20 µm.

FIG. 2 shows a scanning electron microscopic image of a coated PEEK mold after 6 weeks in vivo. The scanning electron microscopic image allows the confirmation of the element-specific composite by means of EDX (energy dispersive X-ray spectroscopy) measurements. Scale: 200 µm.

FIG. 3 shows the same specimen as FIG. 2 in the form of an incident light image of the histological thin section. The incident light image clearly shows the change in the structure of the polymer after the coating procedure and the bone tissue that is anchored to the coating. Scale: 200 µm.

FIG. 4 shows two PEEK-Cages each which were dipped with their lower tip into water that was stained black. On the left side (A) no wetting occurred as the implant has a hydrophobic surface. On the right side (B) wetting occurs strongly after the implant has obtained a hydrophilic surface due to treatment with plasma.

FIG. 5 is a representation of a layer coated according to example 3 by dual spraying by means of a scanning electronic image, on the right of which PEEK and in the middle of which the molten bone substitute material coating can be seen which is about 5 µm thick (Scale 6 µm).

FIG. 6 shows a scanning electron microscopic image of a section of an implant according to the invention (A, scale 2 µm) and an analysis of elements along the horizontal line shown in FIG. 6A (Linescan)(B). The area labeled by vertical lines (positions A and B) is identical in FIG. 6A and FIG. 6B and shows the area of the coated layer. FIG. 6 B shows from top to bottom the shares of carbon, silicium and calcium. It can be seen that the layer has a gradient. The layer is penetrated by the PEEK (carbon) to a higher extend in the lower sections (left in FIGS. 6 A and B) as in the upper sections (right in FIGS. 6 A and B).

Figure 9:
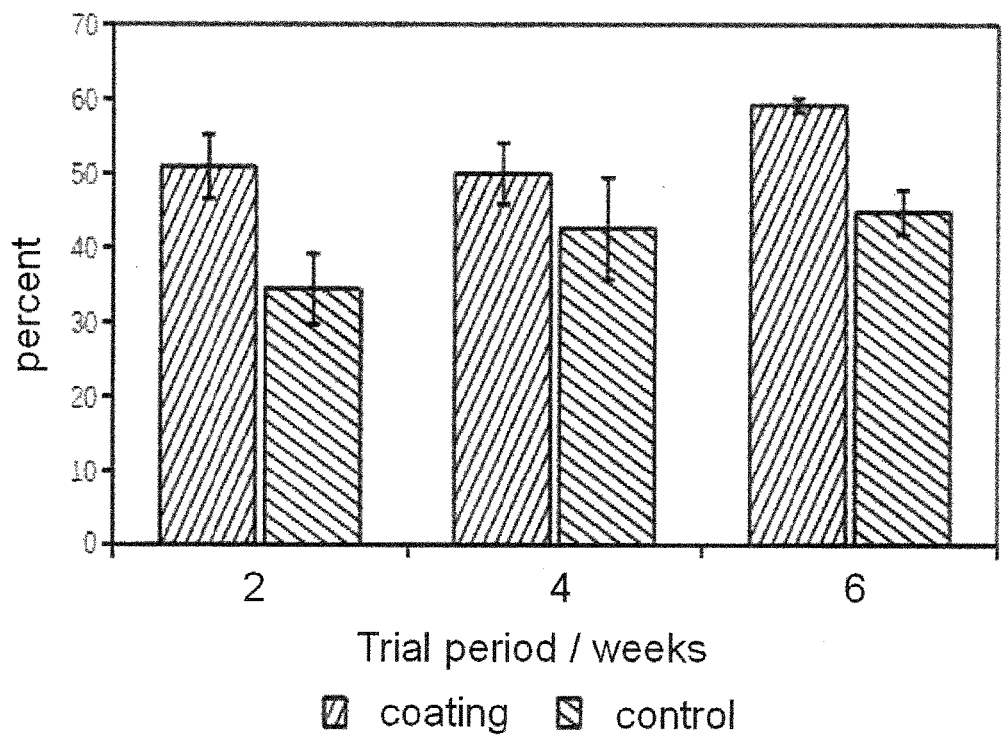

FIG. 9 shows readings of the bone-implant-contact from the in vivo experiment by means of the coating according to the invention in example 2. After 2 weeks resting time an improvement of about 15% of the bone-implant-contact was measured due to the coating, after 4 weeks an improvement of about 10% and after 6 weeks about 15%. The readings were measured with the semi-automatic Axio Vision 4.8 (Zeiss) software.

EXAMPLE 1

Use of a NanoBone® S39-Powder Coating on Rotationally Symmetric PEEK Molds

Figure 1:
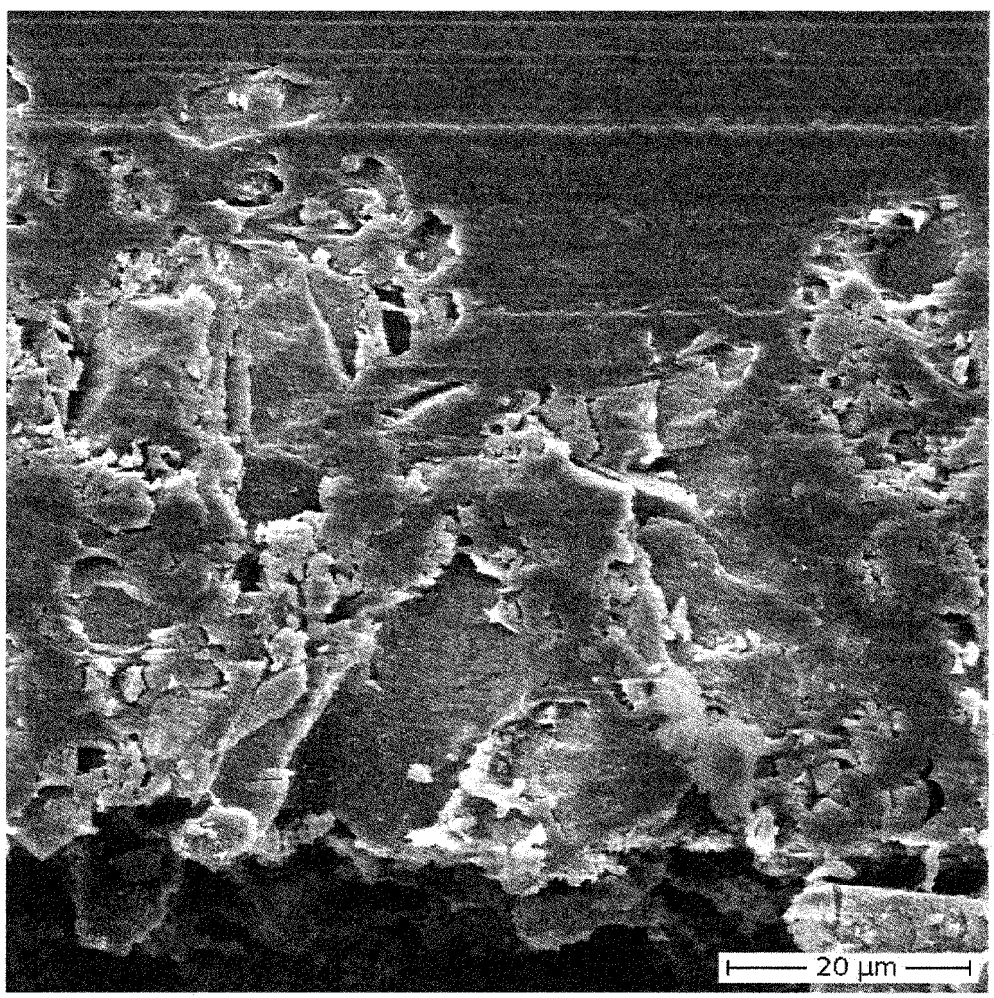
Figure 7:
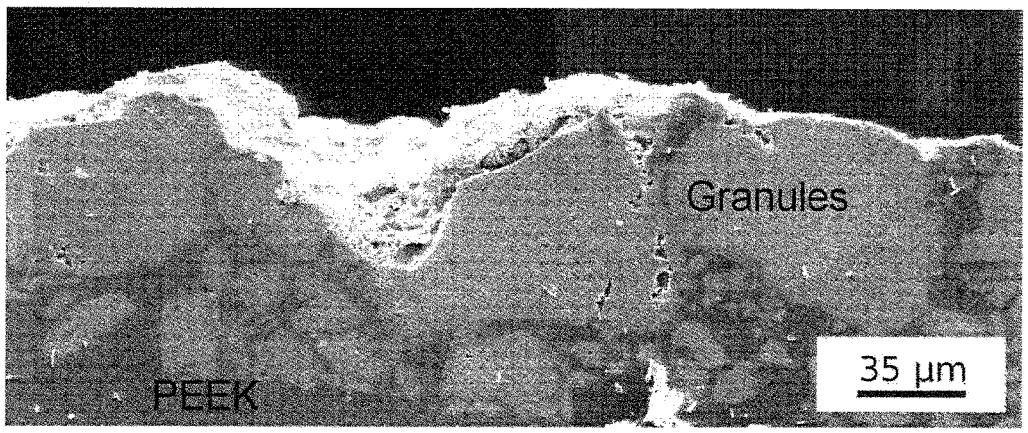
FIG. 7 shows a layer of the bone substitute material manufactured according to example 1 that is partially sunken into PEEK. Scale 35 μm.

NanoBone® S39-granulate (Artoss GmbH, Rostock, Germany, bone substitute material manufactured according to EP 1624904 B1) is ground to a fine powder (particle size 5-100 μm). The PEEK body to be coated is placed in a cylindrical recess (parallel arrangement of the rotational axes of the PEEK body and the recess) that intended especially for this body in a stainless steel mold. The free space between the body to be coated and the metal mold is filled with ground granulate and compressed by means of a little pressure (e.g. about 0.1 to about 5 MPa) in the direction of the rotational axis of the PEEK body. The stainless steel mold (with PEEK body and ground granulate) is then inserted into an induction coil (TIG 30/100, HUTTINGER Elektronik GmbH). Heat can be introduced into the PEEK body very quickly due to the induction process (e.g. 380° C. to 400° C., measured at the surface of the form, for 5 seconds), which only leads to melting of the PEEK surface. The molten PEEK adapts to the nanoporous surface of the NanoBone® and establishes a strong connection. FIGS. 1 and 7 show the sunken layer of biomaterial in the PEEK.

EXAMPLE 2

The molds coated according to example 1, were tested in an in vivo experiment with white New Zealand rabbits with 2, 4 and 6 weeks resting time each with 6 implants in the control group (pure PEEK surface) and 6 implants in the coating group. The implants were inserted laterally in the distal thigh bone. Corresponding experiments often serve the purpose of testing tooth implants in the state of the art. After euthanasia, the implants are processed by means of the thin section technique and stained with toluidine blue, to be able to carry out a histological and histomorphometrical analysis.

The newly nanostructured surface of the PEEK prevents penetration of bone degradating cells, simply due to the new magnitude of the structure in the surface. Also the macroscopic roughness, which is caused by the coating procedure can play a role.

Figure 2:
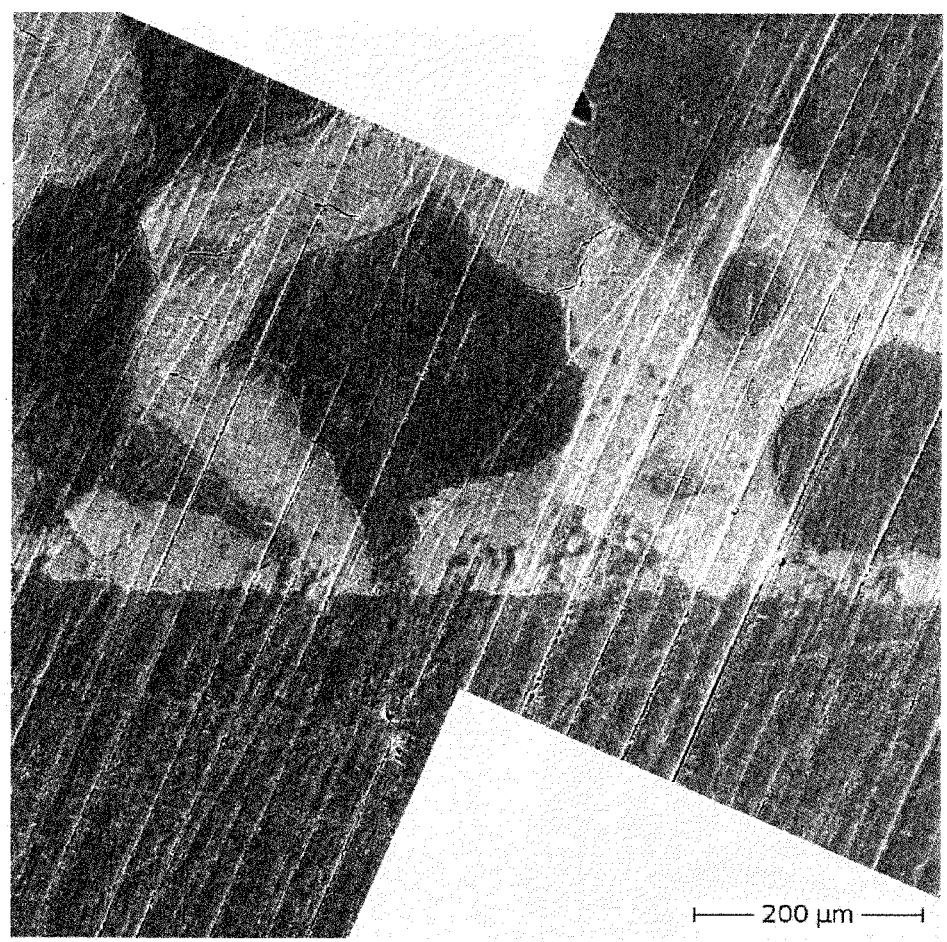
Figure 3:
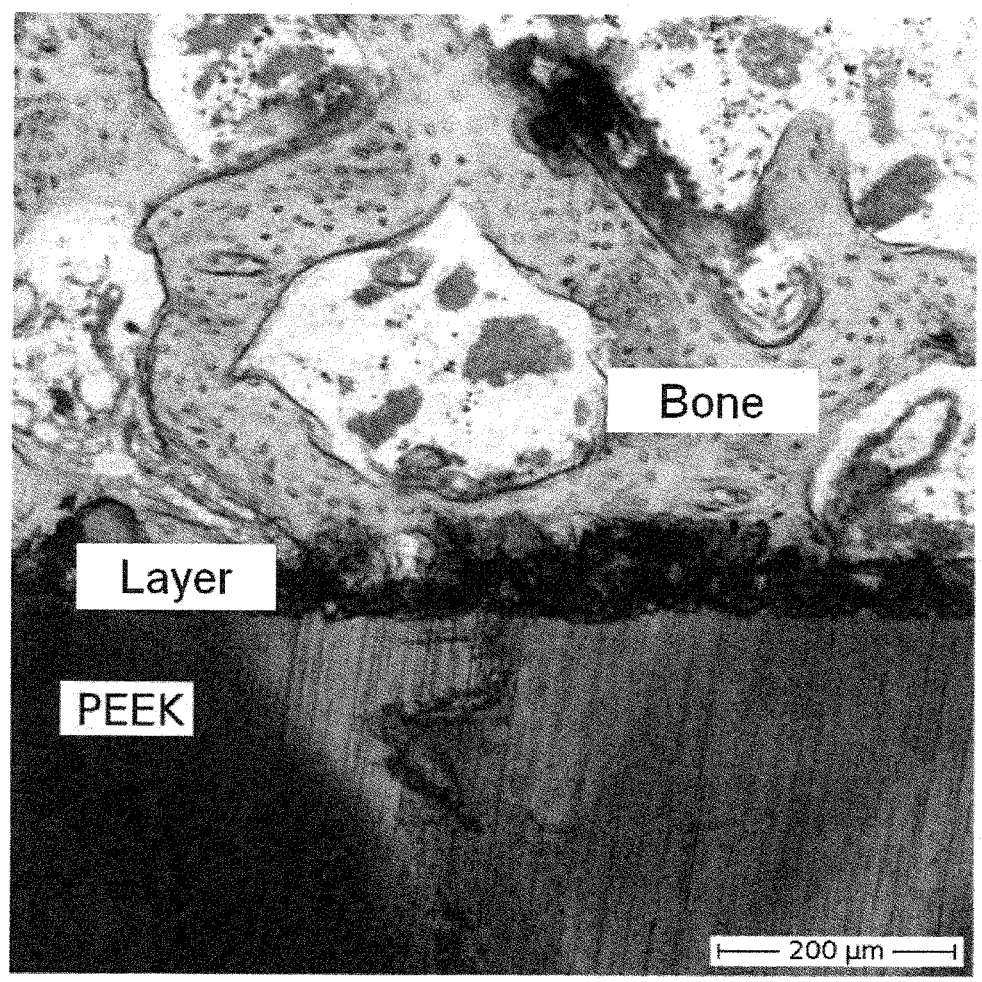

As a consequence, no cell-PEEK interface but only a cellNanoBone® interface exists, wherein the NanoBone® is firmly bound to the PEEK. FIG. 2 shows a scanning electron microscopic image of a coated PEEK mold after 6 weeks in vivo. The scanning electron microscopic image allows confirmation of the element-specific composite by means of EDX measurements. FIG. 3 shows the same specimen as FIG. 2 as an incident light microscopic image of the histological thin section. The incident light microscopic image clearly shows the change in polymer structure due to the coating procedure and the bone tissue anchored to the coating.

Figure 8:
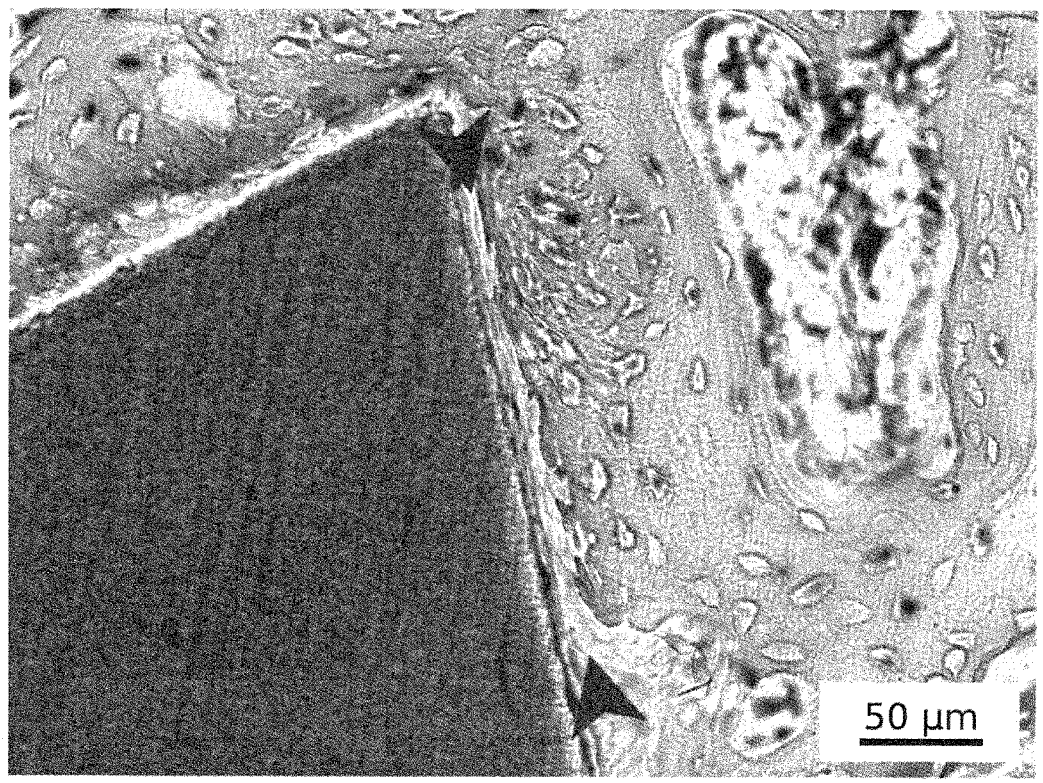
FIG. 8 shows a typical light microscopic image of a histological specimen from the in vivo experiment of example 2 from the control group after 2 weeks. The problem of bad cellular adhesion can be seen from the connective tissue layers between bone tissue and the PEEK implant surface (arrows).

FIG. 8 shows a typical incident light microscopic image of a histological specimen from the control group after 2 weeks. The problem of bad cell adhesion can be seen from the connective tissue layers between the bone tissue and the PEEK-implant-surface (arrows).

The in vivo experiment additionally shows an increase in the bone-implant-contact by about 10-15% (see FIG. 9, measured with the semi-automatic Axio Vision 4.8 (Zeiss) software).

EXAMPLE 3

A silicon dioxide sol is manufactured with the dispersed hydroxyapatite by use of sodium hydrogen phosphate and calcium chloride for the precipitation of HA, by lowering the concentration of the sodium and chlorine ions by means of rinsing and filtering, wherein the ion concentration is reduced to about 0.1% of the initial concentration, by reducing the water content by means of adding and filtering of ethanol, wherein the water content is about 1% of the total solvent. By means of a hydrolysis of tetraethyl ortho silicate (TEOS) using acetic acid as catalyst a silica sol is generated. Ethanol, the sol and the HA suspension are then mixed in such shares that a solid matter content ($SiO_2$ and HA) of 1% and a mass ratio of HA to $SiO_2$ of 76 to 24 develops.

Figure 4:
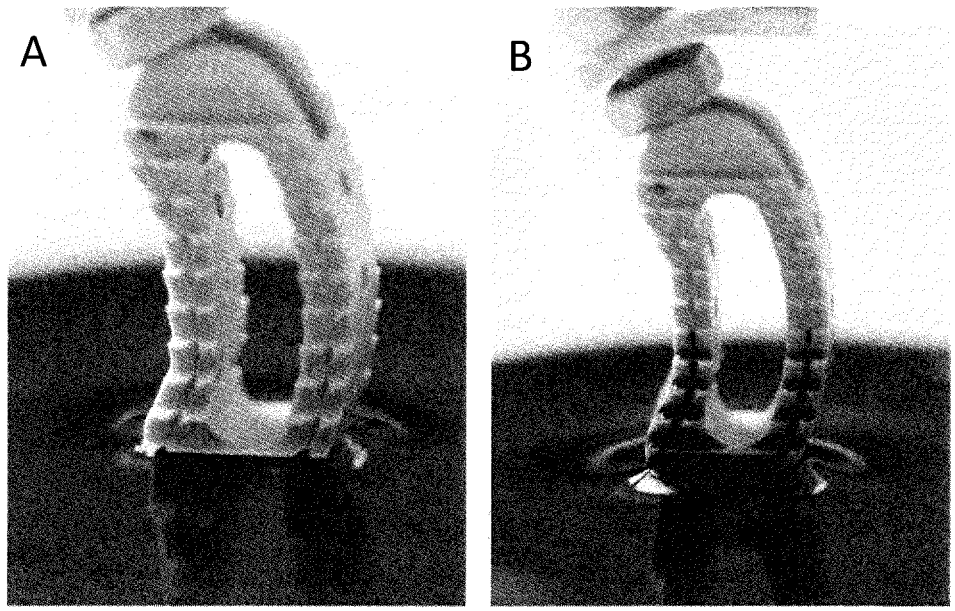

A PEEK implant as used in spinal surgery (cage) is treated in low pressure oxygen plasma for 60 seconds to generate a wetted surface. In FIG. 4 two PEEK cages each were dipped into water stained black with the lower tip. No wetting occurs on the left side because the implant has a hydrophobic surface. On the right strong wetting occurs after the implant has received a hydrophilic surface by means of a plasma treatment.

Afterwards, the PEEK implant is sprayed with the manufactured sol for one second while rotating and dried in the air stream. This is repeated multiple time, e.g. twice or three times, in case this is desired for the layer thickness.

Figure 5:
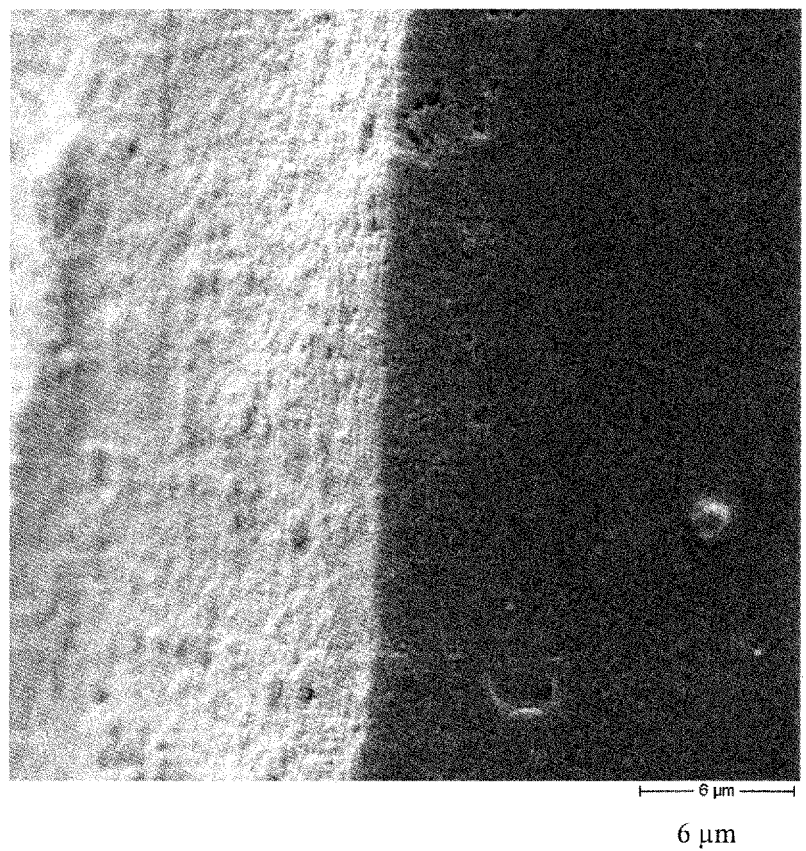
Figure 6:
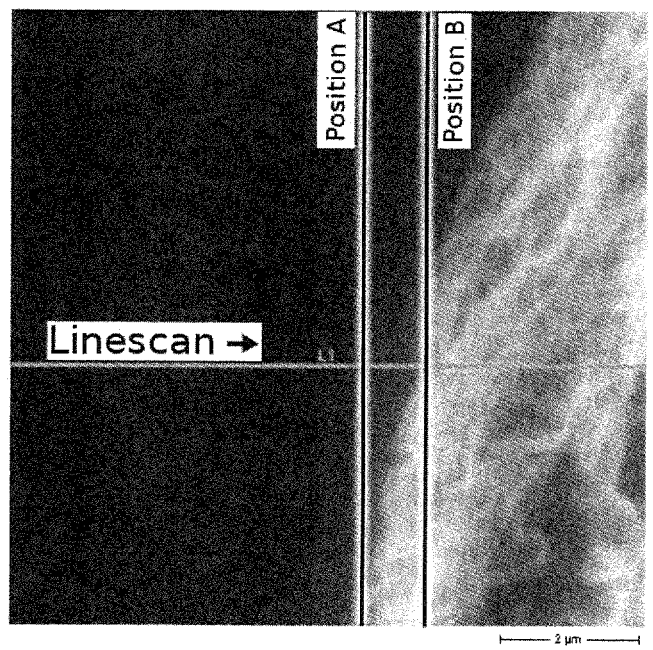
Figure 6:
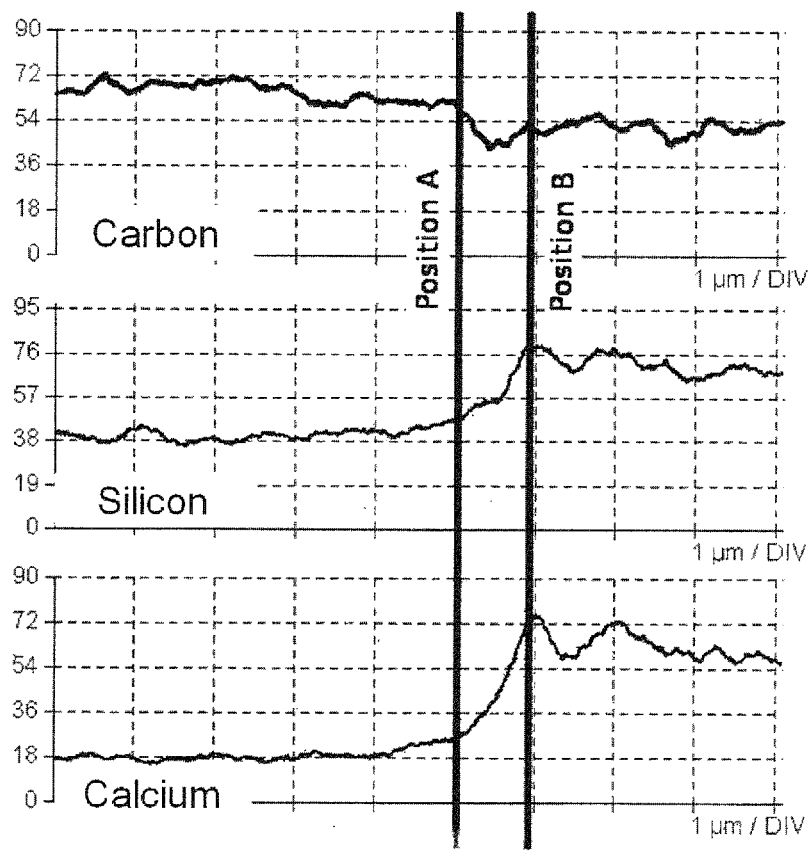

Subsequently, the rotating implant is entered into an air stream having 350°, thus, causing the surface to pass over into the fluid state and "sinking" of the layer. Depiction of the coated layer in FIG. 5 by means of a scanning electron microscopic image. An elemental analysis along the horizontal line (Linescan) was carried out in FIG. 6. The area labeled by vertical lines (position A and B) is identical in the left figure and the diagram on the right and shows the area of the coated layer. The diagram on the right side shows the shares of carbon, silicon and calcium from top to bottom. It can be seen that the layer has a gradient. The layer is penetrated by the PEEK (carbon) to a higher extend in the lower sections (left in the diagram) than in the upper sections (right in the diagram).

Removal of organic remains from the surface of the layer occurs by means of a finalizing oxygen plasma treatment.

The invention claimed is:
1. A method for the manufacture of a plastic implant characterized in that a highly porous bone substitute material is embedded in a surface layer of the plastic implant in the areas in which the bone is to grow onto the implant, wherein the bone substitute material protrudes from the surface, said method being characterized in that:

a mold for the manufacture of the implant is coated with an aqueous slurry of a highly porous bone substitute material in the areas in which the implant is to have contact with the bone;

the layer is dried; and subsequently a plasticized plastic is introduced into the mold.

2. The method for the manufacture of a plastic implant according to claim 1, characterized in that the surface of the plastic is caused to melt.

3. The method for the manufacture of a plastic implant according to claim 1, characterized in that the slurry consists of water and granulate of crystalline hydroxyapatite (HA), embedded in an amorphous porous matrix of silicon dioxide.

4. The method for the manufacture of a plastic implant according to claim 3, wherein the size of the granules is in the range of 1 to 50 μm.

5. A method for the manufacture of a plastic implant characterized in that a highly porous bone substitute material is embedded in a surface layer of the plastic implant in the areas in which the bone is to grow onto the implant, wherein the bone substitute material protrudes from the surface, said method being characterized in that:

the areas of the implant onto which the bone is to grow are hydrophilized;

a layer of silicon dioxide sol in which crystalline hydroxyapatite is dispersed is applied to the hydrophilized areas of the implant, wherein the solid matter concentration (HA and SiO2) of the sol is in the range of 0.2 to 10% by weight, and the ratio of HA to SiO2 is in the range of 90 to 10% by weight to 40 to 60% by weight, then the resulting sol layer is dried, and subsequently the plastic implant surface is heated to an extent that the plastic penetrates into nanopores of the dried sol layer formed.

6. The method for the manufacture of a plastic implant according to claim 5, characterized in that the silicon dioxide sol is manufactured with the dispersed hydroxyapatite by using sodium hydrogen phosphate and calcium chloride for precipitation of HA, wherein the concentration of sodium and chlorine ions is decreased, the water content is reduced to less than 1% of the total solvent, and a silica sol, which is mixed with the hydroxyapatite suspension, is generated by the hydrolysis of tetraethyl orthosilicate (TEOS).

7. The method for the manufacture of a plastic implant according to claim 5, characterized in that the layer of silicon dioxide and HA is activated by an oxygen plasma before or after heating of the plastic implant surface.

8. The method for the manufacture of a plastic implant according to claim 6, wherein the ion concentration is decreased to less than 0.1% of the initial concentration.

9. The method for the manufacture of a plastic implant according to claim 6, wherein an organic acid as catalyst is used for the hydrolysis of TEOS.

10. The method for the manufacture of a plastic implant according to claim 9, wherein the organic acid is acetic acid.

\* \* \* \* \*